United States Patent [19]

Shimura

[11] Patent Number: 5,032,726
[45] Date of Patent: Jul. 16, 1991

[54] METHOD OF RECOGNIZING IRRADIATION FIELD

[75] Inventor: Kazuo Shimura, Kanagawa, Japan

[73] Assignee: Fuji Photo Film Co., Ltd., Kanagawa, Japan

[21] Appl. No.: 523,279

[22] Filed: Mar. 26, 1990

Related U.S. Application Data

[63] Continuation of Ser. No. 181,931, Apr. 15, 1988, abandoned.

[30] Foreign Application Priority Data

Apr. 15, 1987 [JP] Japan ................................. 62-92759

[51] Int. Cl.⁵ ............................................ G01N 23/04
[52] U.S. Cl. ................... 250/327.2; 250/484.1
[58] Field of Search ................... 250/327.2, 484.1; 382/22, 25

[56] References Cited

U.S. PATENT DOCUMENTS 4,685,143 8/1987 Choate .................................... 382/25

FOREIGN PATENT DOCUMENTS 0170270 2/1986 European Pat. Off. ......... 250/327.2

OTHER PUBLICATIONS

Pratt, W., *Digital Image Processing*, p. 523, John Wiley (1978).

*Primary Examiner*—Jack I. Berman
*Assistant Examiner*—Richard Hanig
*Attorney, Agent, or Firm*—Sughrue, Mion, Zinn, Macpeak & Seas

[57] ABSTRACT

In a method of recognizing an irradiation field on a recording region of a recording medium on which one or more radiation image is recorded by limitation of the irradiation field, the recording region is divided into a plurality of small regions and the irradiation field is recognized for each of the small regions on the basis of image signals corresponding to the small region.

20 Claims, 2 Drawing Sheets

METHOD OF RECOGNIZING IRRADIATION FIELD

This is a continuation of application Ser. No. 181,931, filed Apr. 15, 1988, now abandoned.

BACKGROUND OF THE INVENTION

1. Field of the Invention

This invention relates to a method of recognizing an irradiation field in the case where a radiation image is recorded on a recording medium such as a stimulable phosphor sheet by limitation of the irradiation field of a radiation.

More particularly, this invention relates to a method of recognizing the irradiation field which can be effectively applied to both a case where only a single radiation image is recorded on one recording medium (This will be referred to as "single recording", hereinbelow.) and a case where the recording region on one recording medium is divided into a plurality of subdivisions and a plurality of radiation images are recorded on the respective subdivisions (This will be referred to as "subdivision image recording", hereinbelow.).

2. Description of the Prior Art

When certain kinds of phosphors are exposed to a radiation such as X-rays, α-rays, β-rays, γ-rays, cathode rays or ultraviolet rays, they store a part of the energy of the radiation. Then, when the phosphor which has been exposed to the radiation is exposed to stimulating rays such as visible light, light is emitted by the phosphor in proportion to the stored energy of the radiation. A phosphor exhibiting such properties is referred to as a stimulable phosphor.

As disclosed in U.S. Pat. No. 4,258,264 and Japanese Unexamined Patent Publication No. 56(1981)-11395, it has been proposed to use a stimulable phosphor in a radiation image recording and reproducing system. Specifically, a sheet provided with a layer of the stimulable phosphor (hereinafter referred to as a stimulable phosphor sheet) is first exposed to a radiation passing through an object such as the human body to have a radiation image of the object stored thereon, and is then exposed to stimulating rays such as a laser beam which cause the stimulable phosphor sheet to emit light in proportion to the stored radiation energy. The light emitted by the stimulable phosphor sheet upon stimulation thereof is photoelectrically detected and converted into an electric image signal, image processing is carried out on the electric image signal, and the radiation image of the object is reproduced as a visible image by use of the processed image signal on a recording medium such as a photographic film, a display device such as a cathode ray tube (CRT), or the like.

In the aforesaid radiation image recording and reproducing system, the level of the radiation energy stored on the stimulable phosphor sheet is caused to fluctuate among radiation images by changes in the object, the image recording portion thereof, radiation dose, or the like.

However, in the aforesaid radiation image recording and reproducing system, characteristics of the stored image information of each radiation image, particularly the level of the radiation energy or the like of each radiation image stored on the stimulable phosphor sheet, may be ascertained in advance, and the light emitted by the stimulable phosphor sheet may be photoelectrically detected by use of read-out conditions such as a read-out gain and a scale factor adjusted to appropriate values in accordance with the characteristics of the stored image information of each radiation image. In this case, for each radiation image, it becomes possible to obtain a visible image free from adverse effects of the fluctuation in the level of the radiation energy stored on the stimulable phosphor sheet and suitable for viewing, particularly for diagnostic purposes, for example, a visible image wherein the necessary object image information is always expressed within the correct density range suitable for viewing, particularly for diagnostic purposes.

Also, in the aforesaid radiation image recording and reproducing system, image processing of the image signal detected photoelectrically is carried out by use of image processing conditions such as gradation processing conditions adjusted for each radiation image based on the image recording portion of the object such as the head, chest or abdomen, and/or the image recording method such as plain image recording or contrasted image recording so that a visible image suitable for viewing, particularly for diagnostic purposes, can be obtained. However, for example, in the case where detection of the image signal is carried out without using the read-out conditions adjusted in accordance with the characteristics of the stored image information of each radiation image, the image processing conditions should preferably be adjusted by considering the characteristics of the stored image information of each radiation image, which have been ascertained in advance, besides the image recording portion of the object and/or the image recording method. In this manner, it becomes possible to obtain a visible image suitable for viewing, particularly for diagnostic purposes, wherein the necessary object image information is expressed within the correct density range.

Ascertaining of the characteristics of the image information stored on the stimulable phosphor sheet prior to the image read-out and image processing may be carried out by use of the method as disclosed in U.S. Pat. No. 4,527,060. In the disclosed method, a read-out operation for ascertaining the image information of a radiation image stored on the stimulable phosphor sheet (hereinafter referred to as the preliminary read-out) is carried out in advance by use of stimulating rays having stimulation energy of a level lower than the level of the stimulation energy of stimulating rays used in a read-out operation for obtaining a visible image for viewing, particularly for diagnostic purposes (hereinafter referred to as the final read-out), and thereafter the final read-out is carried out. The characteristics of the stored image information are ascertained based on the image information (preliminary read-out image signal) obtained by the preliminary read-out.

As mentioned above, the level of the stimulating rays used in the preliminary read-out is lower than the level of the stimulating rays used in the final read-out. Specifically, the effective energy of the stimulating rays which the stimulable phosphor sheet receives per unit area in the preliminary read-out should be lower than the effective energy of the stimulating rays used in the final read-out.

Another approach to the ascertaining of the characteristics of the image information stored on the stimulable phosphor sheet prior to image processing is to ascertain it based on the image information (image signal) detected by the final read-out. Though the characteristics of the stored image information ascertained in this manner cannot be used for adjusting the read-out conditions in the final read-out, they can be used for adjusting the image processing conditions. This method is effective in the radiation image recording and reproducing system wherein the preliminary read-out is not carried out.

Various methods have been proposed for ascertaining the characteristics of the stored image information based on the preliminary read-out image signal obtained by the preliminary read-out or the final read-out image signal obtained by the final read-out. As one of such methods, it has heretofore been known to utilize a histogram of the image signals (image signal levels). With this method, the characteristics of the stored image information may be ascertained based on, for example, the maximum signal value, the minimum signal value, or a signal value at which the frequency is the maximum in the histogram. Therefore, it becomes possible to reproduce a visible image having an improved image quality, particularly a high diagnostic efficiency and accuracy, by adjusting the final read-out conditions such as the read-out gain and the scale factor and/or the image processing conditions such as the gradation processing conditions and the frequency response processing conditions based on the maximum signal value, the minimum signal value, a signal value at which the frequency is the maximum, or the like in the histogram.

On the other hand, in the course of radiation image recording, it is often desired that portions of the object not related to diagnosis or the like be prevented from exposure to a radiation. Further, when the object portions not related to diagnosis or the like are exposed to a radiation, the radiation is scattered by such portions to the portion related to diagnosis or the like, and the contrast and resolution are adversely affected by the scattered radiation. Therefore, in many cases, the irradiation field is limited to an area smaller than the overall recording region on the stimulable phosphor sheet when a radiation image is recorded.

However, when the characteristics of the image information stored on the stimulable phosphor sheet are ascertained based on the histogram of the image signals, the problem as described below arises. As shown in FIG. 9, when an irradiation field 14 is limited to an area smaller than an image recording region 12 on a stimulable phosphor sheet 10 (In the case of the sheet 10 shown in FIG. 9, the image recording region 12 covers the whole area of the sheet 10.) and the preliminary read-out or the final read-out is carried out over an area markedly larger than the irradiation field 14, for example, over the overall image recording region 12 on the stimulable phosphor sheet 10, the characteristics of the image information actually stored within the irradiation field 14 are ascertained incorrectly. Specifically, in the aforesaid case, since the image signals at regions outside of the irradiation field 14 are also included in the histogram, the histogram does not accurately represent the actual image information stored within the irradiation field 14.

Therefore, in the case where radiation image recording is carried out by limiting the irradiation field, the characteristics of the stored image information are to be ascertained based on the preliminary read-out image signal or the final read-out image signal by the method as mentioned above, and the final read-out conditions and/or the image processing conditions are to be adjusted based on the ascertained characteristics, the irradiation field should be recognized and the characteristics of the stored image information should be accurately ascertained based only on the image signal within the irradiation field, thereby to eliminate adverse effects of the scattered radiation outside of the irradiation field.

Besides the case wherein the read-out conditions and/or the image processing conditions are to be adjusted for a radiation image stored on the stimulable phosphor sheet, recognition of the irradiation field is also necessary for various purposes in the case where a radiation image is recorded on a recording medium by limitation of the irradiation field.

The applicants have proposed various methods of recognizing the irradiation field 14 as disclosed in, for example, U.S. Pat. No. 4,851,678. However, though those methods can be suitably applied in the case of the single recording where only a single radiation image is recorded on one single recording medium and accordingly, only one irradiation field is on the recording medium, most of them are difficult to apply in the case of the subdivision image recording where a plurality of radiation images are recorded on a plurality of respective subdivisions of one recording medium with the irradiation field being limited for each recording and accordingly, a plurality of irradiation fields are on the recording medium.

For example, as a method of recognizing the irradiation field, there has been proposed an algorism utilizing Hough conversion. In the algorism, prospective edge points which are considered to be edge (contour) portions of the irradiation field on the recording medium are detected from image signals read out from the recording region of the recording medium, curves represented by formula $$\Sigma = x_o \cos \theta + y_o \sin \theta$$

are obtained for the respective prospective points wherein $x_o$ and $y_o$ respectively represent the x coordinate (constant) and the y coordinate (constant) of a given prospective point when the positions of the prospective points are expressed with an x-y orthogonal coordinate system, straight lines defined by formula $$\rho_o = x \cos \theta_o + y \sin \theta_o$$

in the orthogonal coordinate system (straight lines along the prospective points, e.g., straight lines $1_1$ to $1_4$ in FIG. 9) are obtained on the basis of the intersections of the curves thus obtained, and the regions surrounded by the straight lines or the regions surrounded by the straight lines and the outer edge of the recording region (in the case that the irradiation field 14 is positioned as shown in FIG. 10 with respect to the recording region 12 of the recording medium) are recognized as the irradiation field.

In this algorism, there can be a plurality of regions surrounded by the straight lines obtained by Hough conversion or by the straight lines and the outer edge of the recording region, and sometimes which region is the true irradiation field must be determined. For example, which region is the true irradiation field can be determined by detecting the center point of the recording region or the center of density (image signal level) gravity and recognizing the region including the center point or the center of density gravity as the irradiation center.

However, though the center point of the recording region or the center of density gravity is inherently positioned in the irradiation field in the case of the single recording, they are apt to be positioned outside the irradiation fields in the case of the subdivision image recording. Particularly, the center of density gravity can be positioned only in one of the irradiation fields in the case of the subdivision image recording.

Accordingly, though the irradiation field recognizing algorism can be suitably applied in the case of the single recording, a region outside the irradiation field can be mistaken for the irradiation field or only one of the irradiation fields can be recognized when the algorism is applied in the case of the subdivision image recording. That is, the algorism can be applied only when it is known in advance that the recording on a given recording medium is the single recording, and when the recording on a given recording medium is the subdivision image recording, or when it is not known which of the single recording and the subdivision image recording has been made on a given recording medium, the algorism is difficult to apply.

SUMMARY OF THE INVENTION

The primary object of the present invention is to provide a method of recognizing an irradiation field in which the irradiation field can be effectively recognized irrespective of whether the recording o the recording medium is the single recording or the subdivision image recording on the basis of various algorisms including such an algorism that can conventionally be applied only in the case of the single recording.

In accordance with the present invention, there is provided a method of recognizing an irradiation field on a recording region of a recording medium on which one or more radiation image is recorded by limitation of the irradiation field including a step of recognizing the irradiation field on the basis of image signals detected from the recording region, characterized in that said recording region is divided into a plurality of small regions and the irradiation field is recognized for each of the small regions on the basis of the image signals corresponding to the small region.

By the term "recording medium" as used herein is meant a medium capable of recording a radiation image thereon, such as a stimulable phosphor sheet. However, the recording medium is not limited to the stimulable phosphor sheet.

By the term "image signals detected from the recording region" are meant signals detected by reading out a radiation image recorded on the recording region by any method, for example, image signals detected by the preliminary read-out or the final read-out from the stimulable phosphor sheet. However, said image signals are not limited to those detected in this manner from the stimulable phosphor sheet.

The recording region should be divided into a plurality of small regions so that only one irradiation field exists in each of the small regions so long as the number of the subdivision on a given recording medium is normal. In the case of the normal subdivision image recording, the number of the subdivisions on the recording medium is two or four. That is, normally, the recording region is laterally or longitudinally divided into two subdivisions or is laterally and longitudinally bisected into four subdivisions. Accordingly, the recording region should be divided into at least four regions.

Recognition of the irradiation field for each of the small regions on the basis of the image signals corresponding to the small region may be effected by use of various algorism without being limited to a particular algorism.

Of course, the method of utilizing the irradiation field recognized in accordance with the present invention is not limited to a particular one.

By dividing the recording region into a plurality of small regions so that only one irradiation field exists in each small region and by recognizing the irradiation field for each of the small regions, it becomes feasible to recognize the irradiation field irrespective of whether the recording on the recording medium is the single recording or the subdivision image recording by use of even an algorism which can conventionally be applied only in the case of the single recording.

Further, the method in accordance with the present invention is advantageous in that the irradiation field can be recognized with ease irrespective of the shape of the irradiation field and the number of the subdivisions on the recording medium.

DESCRIPTION OF THE PREFERRED EMBODIMENTS

An embodiment of the present invention in which the irradiation field is recognized from the preliminary read-out image signals will be described with reference to the drawings, hereinbelow.

Figure 1:
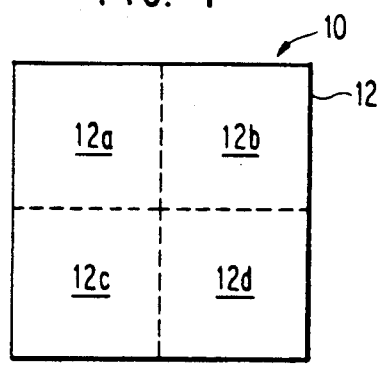
FIG. 1 is a view for illustrating an example of the manner for dividing the recording region into a plurality of small regions in order to carry out the method of the present invention.

In this embodiment, the preliminary read-out is first carried out on a stimulable phosphor sheet 10, shown in FIG. 1, carrying a radiation image information recorded thereon by limitation of the irradiation field. That is, the stimulable phosphor sheet 10 is two-dimensionally scanned by stimulating rays having stimulating energy of a level lower than the level of the stimulation energy of stimulating rays used in the final read-out, and light emitted by the stimulable phosphor sheet 10 upon stimulation is detected by a photodetector such as a photomultiplier which outputs preliminary read-out image signal.

Thereafter, the recording region 12 of the stimulable phosphor sheet 10 (The recording region 12 covers the whole area of the surface of the sheet 10 in this particular embodiment.) is laterally and longitudinally bisected into four small regions 12a to 12d. As can be understood from FIG. 2, by dividing the recording region 12 in this manner, each small region inherently has one and only one irradiation field irrespective of the number of radiation images recorded on the recording region 12 so long as the number of the radiation images does not exceed four. In FIGS. 2(a) to 2(d), reference numerals 14a to 14d denote the irradiation fields in the respective small regions 12a to 12d.

If the number of the radiation images can exceed four, i.e., if the subdivision image recording can be carried out with the recording region 12 being divided into more than four subdivisions, the recording region 12 must be divided into at least like number of small regions. However, normally, the number of radiation images to be recorded on one stimulable phosphor sheet 10 is four at most.

After dividing the recording region 12 into the small regions 12a to 12d, the irradiation fields 14a to 14d in the respective small regions 12a to 12d are detected from image signals corresponding to the respective small regions 12a to 12d. The detection of the irradiation field for each small region may be carried out according to any of suitable algorisms.

As an example of suitable algorisms, an algorism utilizing Hough conversion will be described in conjunction with detection of the irradiation field 14a in the small region 12a. For the purpose of generalization, it is assumed that the irradiation field 14a in the small region 12a is polygonal in shape as shown in FIG. 3.

Figure 3:
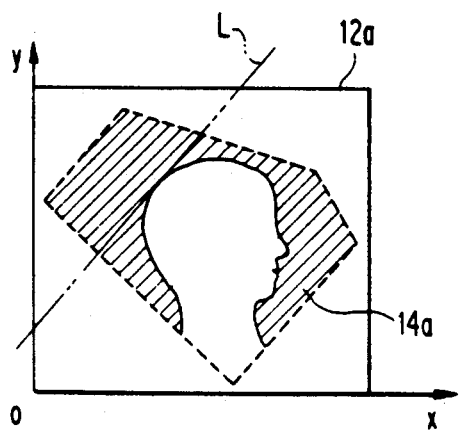
FIG. 3 is a view for illustrating the prospective edge points.

First an x-y orthogonal coordinate system is defined as shown in FIG. 3 with respect to the small region 12a. Thereafter, prospective edge points which are considered to be on the edge of the irradiation field 14a as shown by the broken line in FIG. 3 are detected. Such prospective edge points can be detected, for instance, by differentiating the image signals corresponding to the small region 12a.

Generally, the level of the image signals corresponding to the picture elements in the irradiation field is high while the level of the image signals corresponding to the picture elements outside the irradiation field is low. Accordingly, when the image signals are differentiated, the absolute values of the differential values become larger at the edge portion of the irradiation field than at the other portions. Accordingly, picture elements corresponding to the differential values having the absolute value larger than an appropriate threshold value may be considered to be the prospective edge point. The differentiation may be one-dimensional linear or higher differentiation or two-dimensional linear or higher differentiation. In the case of a discretely sampled image, differentiation is equivalent to calculation of the differences between image signals corresponding to picture elements near to each other.

Figure 4:
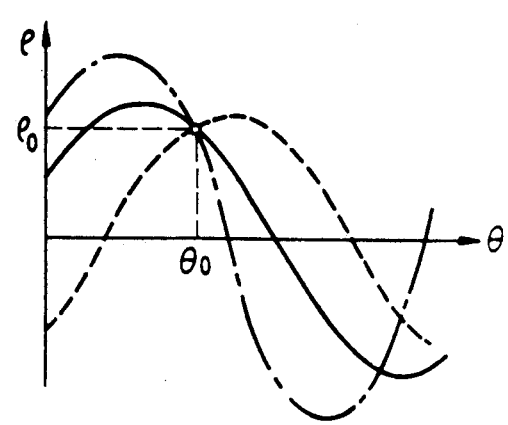
FIGS. 4 and 5 are views for illustrating the curves and the straight lines to be obtained by Hough conversion.

After thus detected the prospective edge points, curves represented by formula $$\rho = x_o \cos \theta + y_o \sin \theta$$

are obtained for the respective prospective points wherein $x_o$ and $y_o$ respectively represent the x coordinate (constant) and the y coordinate (constant) of a given prospective point when the positions of the prospective points are expressed with an x-y orthogonal coordinate system. These curves are as shown in FIG. 4 and the number of the curves is equal to the number of the prospective edge points.

Then points ($\rho_o$, $\theta_o$) at which more than a predetermined number Q of the curves intersect each other are obtained. Practically, numbers of the curves cannot intersect each other strictly at one point due to errors in the detected coordinates ($x_o$, $y_o$) of the prospective edge points and the like. Accordingly, when a plurality of intersections of a pair of the curves exist spaced from each other within a predetermined very small distance, the center of such intersections is regarded as the intersections ($\rho_o$, $\theta_o$).

Figure 5:
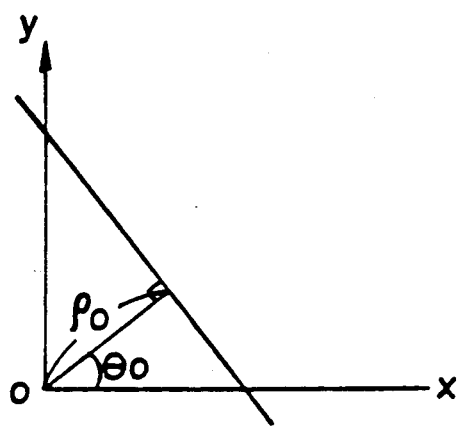

Then straight lines defined by formula $$\rho_o = x \cos \theta_o + y \sin \theta_o$$

in the orthogonal coordinate system (See FIG. 5) are obtained on the basis of the intersections of the curves thus obtained. The straight lines pass a plurality of the prospective edge points ($x_o$, $y_o$). Points corresponding to the edge portion of a bone image sometimes can be detected as the prospective edge point. In this case, a straight line L (FIG. 3) joining true prospective edge points and the point on the edge portion of the bone image which is mistaken for the prospective edge point of the irradiation field can be obtained. However, this can be obtained by setting the predetermined number Q to be sufficiently large (e.g., 20). That is, only straight lines passing through a number of the prospective edge points can be obtained.

Figure 6:
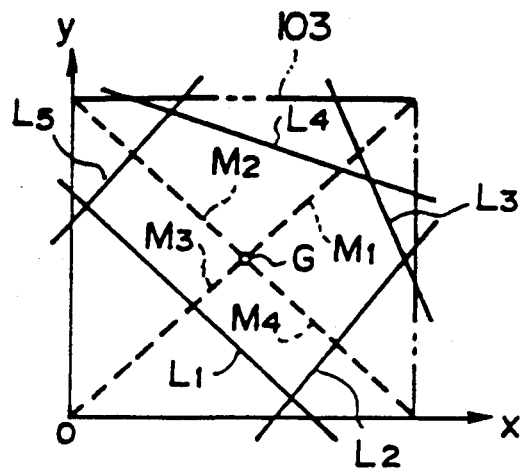
FIG. 6 is a view for illustrating the method of recognizing the irradiation field.
Figure 7:
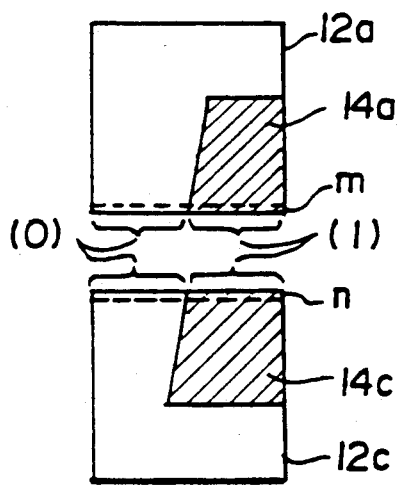
FIGS. 7 and 8 are views for illustrating the method of determining whether the irradiation fields in adjacent two small regions are merged with each other.

The relevant straight lines are as shown in FIG. 7 when the prospective edge points are distributed as shown in FIG. 3. Then the region surrounded by the straight lines L1, L2, L3 ... Ln thus obtained is recognized as the irradiation field 14a. Recognition of the region surrounded by the straight lines is effected in the following manner, for example. Straight lines M1, M2, M3 ... Mm (FIG. 6) joining the respective corners of the small region 12a and the center G of the small region 12a (When the small region 12a is rectangular, the straight lines are four in number.) have been stored in a memory, and then whether there is an intersection of the lines M1 to Mm and a given one of the lines L1 to Ln is detected When there is an intersection, the part of the small region on the side of the given one of the lines L1 to Ln including the corresponding corner of the small region 12a is cut. When this operation is carried out for all the lines L1 to Ln, the region surrounded by the lines L1 to Ln will remain.

Figure 2A:
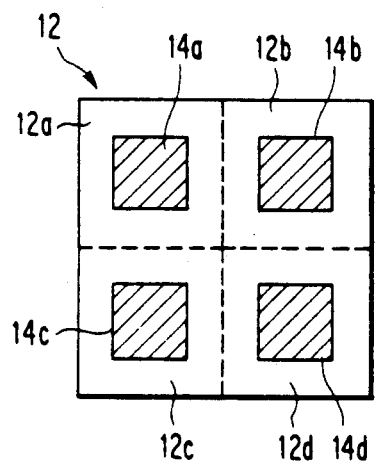
FIGS. 2(a) to 2(c) are views for illustrating various relations between the small regions of the recording region and the irradiation field.
Figure 2B:
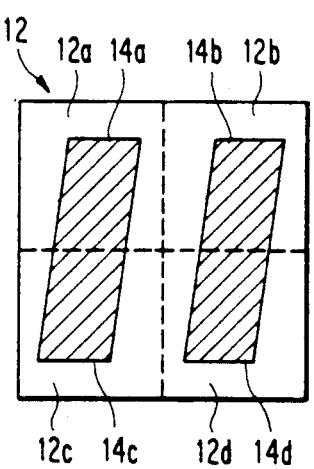

Though, in the case of the small region 12a shown in FIG. 2(a), the irradiation field 14a does not reach the outer edge of the small region 12a, the irradiation field 14a reaches the outer edge of the small region 12a in the case of that shown in FIG. 2(b). In this case, the irradiation field 14a is recognized as the region surrounded by the three straight lines obtained by Hough conversion and the line defining the lower edge of the small region 12a. Also the recognition of the region in this case may be effected in the manner described above. However, in this case, the center G of the small region 12a can be outside the irradiation field 14a. Accordingly, the center of density (image signal level) gravity G' may be used instead of the center G and instead of the straight lines M1, M2, M3 ... Mm joining the respective corners of the small region 12a and the center G of the small region 12a, straight lines joining the respective corners of the small region 12a and the center of density gravity G' may be used. The coordinates ($\bar{x}$, $\bar{y}$) of the center of density gravity G' is represented by the following formulae.

$$x = \Sigma[f(x_i, y_i) \times x_i] / \Sigma f(x_i, y_i)$$

$$y = \Sigma[f(x_i, y_i) \times y_i] / \Sigma f(x_i, y_i)$$

wherein $f(x_i, y_i)$ represents the image signal level of a given picture element $(x_i, y_i)$.

By detecting the irradiation fields of the respective small regions as described above and combining the result of the detections, all the irradiation fields on the stimulable phosphor sheet can be precisely recognized.

The irradiation field recognized in the manner described above may be utilized for various purposes. For example, only the image information inside of the irradiation field may be extracted from the final read-out image information to be obtained after the preliminary read-out and stored in order to speed up the subsequent signal processing. Further, only the image information inside of the irradiation field may be extracted from the preliminary read-out image information, and the read-out conditions and/or the image processing conditions for the final read-out may be determined on the basis of the extracted preliminary read-out image information, e.g., the histogram of the extracted preliminary read-out image information (the image signal level).

Figure 2C:
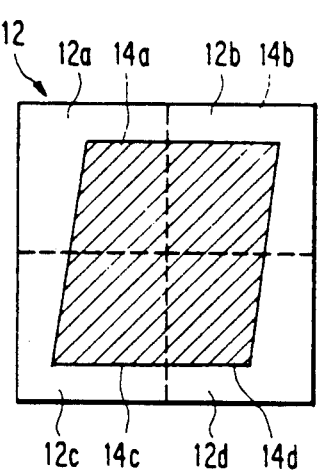

When determining the read-out conditions or the like, sometimes it is preferred that whether the irradiation fields in the respective small regions are merged with each other as in the case shown in FIG. 2(c) or are separated from each other as in the case shown in FIG. 2(a) be detected, and when they are separated from each other, the read-out conditions and the like be separately determined for each irradiation field on the basis of the image information inside the corresponding irradiation field.

For example, whether the irradiation fields are merged with each other can be detected in the following manner.

For example, when detecting whether the irradiation fields 14a and 14c in the small regions 12a and 12c are merged together in the case shown in FIG. 2(c), the picture elements in the picture element rows m and n on the adjacent outer edges (i.e., on the division line) of the small regions 12a and 12c are encoded into 1 (when the element is inside the irradiation field) or 0 (when the element is outside the irradiation field), and the logical sum of the binary codes of the opposed picture elements in the picture element rows m and n are calculated. ($0\times0=1$, $0\times1=0$, $1\times0=0$, $1\times1=1$) When the number of opposed picture elements which give the logical sum of 1 exceeds a predetermined % of the number of all the picture elements on the picture element rows m and n, it is determined that the irradiation fields 14a and 14c are merged with each other. This method, after all, detects how near the edges of the irradiation fields 14a and 14c are positioned to each other on the division line, and when the edges of the irradiation fields are positioned nearer than a predetermined degree, it is determined that the two irradiation fields are merged with each other.

Figure 8:
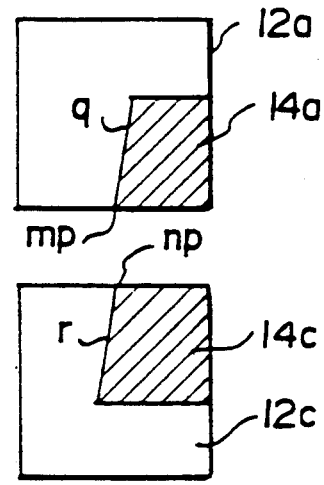
Figure 9:
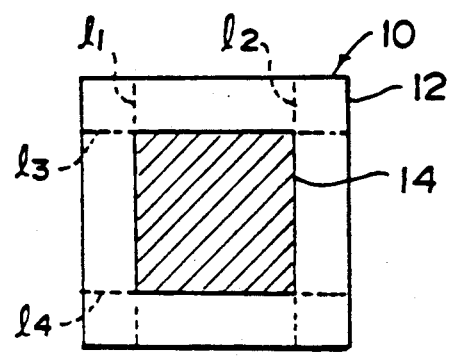
FIG. 9 and 10 are views respectively showing different examples of the irradiation field in the case of the single recording.
Figure 10:
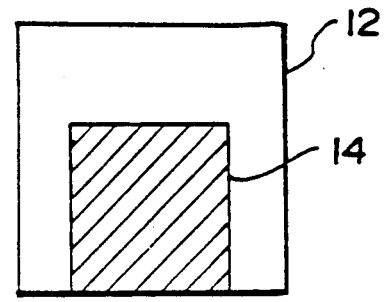

In another method, the coordinates of the intersection mp of the division line and an edge g of the irradiation field 14a and the coordinates of the intersection np of the division line and an edge r of the irradiation field 14c are obtained as shown in FIG. 8 and the distance therebetween is calculated. When the proportion of the distance to the length of the division line is smaller than a predetermined value, it is determined that the irradiation fields 14a and 14c are merged with each other.

Further, it may be determined that the irradiation fields 14a and 14c are merged with each other when the intercept and the inclination of the equation representing the edge g of the irradiation field 14a are substantially equal to those of the equation representing the edge r of the irradiation field 14c.

Though, in the embodiment described above, prospective edge points of the irradiation field are obtained, lines passing through the prospective edge points are obtained by Hough conversion, and the region surrounded by the lines thus obtained or by the lines and the outer edge of the recording region is recognized as the irradiation field, the lines passing through the prospective edge points may be obtained by various methods other than Hough conversion. For example, the lines passing through the prospective edge points may be obtained by smoothing the prospective edge points and joining points lingering after the smoothing, or by locally applying the least squares method to obtain a plurality of straight lines and connecting the lines, or by applying spline curves.

The prospective edge points of the irradiation field can be obtained by differentiating image signals as described above. Also this differentiation may be carried out in various manners. For example, differentiation may be carried out radially outwardly in a plurality of directions from a predetermined point in the irradiation field. As the predetermined point in this case, the center of density gravity, the maximum density point or the center of density gravity on the higher density side obtained by binary-coding the density may be employed.

Though, in the embodiment described above, the irradiation field is recognized on the basis of the preliminary read-out image information, the present invention may be applied to the system in which the irradiation field is recognized on the basis of the final read-out image information. In the latter case, the irradiation field recognized can be utilized for determining the image processing conditions from the final read-out image information, for example.

It should be understood that the present invention can be modified in various manners within its scope, and is not limited to the embodiments described above.

I claim:

1. A method of detecting an irradiation portion of a recording region of a recording medium on which at least one radiation image is recorded with said irradiation portion being contained within said recording region, said irradiation portion being either a single irradiation field or a plurality of irradiation fields, the method comprising the steps of:

scanning said recording region to photoelectrically detect radiation images stored therein, said recording region emitting light in proportion to said radiation stored in said recording region;

detecting and converting photoelectrically said emitted light into electric image signals;

designating a plurality of sections of said recording region as subdivisions each for receiving a single irradiation field; and processing independently electric image signals corresponding to radiation detected from each of said subdivisions to detect the boundary of an irradiation field within each of said subdivisions.

2. A method according to claim 1, wherein said processing step comprises for each subdivision:

detecting photoelectrically prospective edge points of any irradiation field therein;

connecting said prospective edge points of said irradiation field by passing lines through said prospective edge points of said irradiation field; and recognizing said irradiation field as a region surrounded by one of either said lines or said lines and an outer edge of said subdivision.

3. A method according to claim 1, wherein said method further comprises a step of storing results of each detection of said electric image signals of said each subdivision in a memory means and combining the results of the separate detections.

4. A method according to claim 1, wherein said method further comprises a step of identifying a first irradiation field within a first subdivision merged with a second irradiation field in an adjacent, second subdivision.

5. A method according to claim 4, wherein said identifying step comprises the steps of:
encoding picture elements in picture element rows on adjacent outer edges of said first and second subdivisions;
comparing the values of codes of opposed picture elements in opposed picture element rows of said first and second subdivisions; and
determining said first and second irradiation fields are merged based upon a number of opposed picture elements which are both in an irradiation field exceeding a predetermined number.

6. A method according to claim 4, wherein said identifying step is made based upon a distance apart of said first and second irradiation fields, said first and second irradiation fields being merged when said distance is smaller than a predetermined value.

7. A method according to claim 4, wherein said identifying step is made based upon an intercept and inclination of an equation representing an edge of said first irradiation field being substantially equal to those of an equation representing an edge of said second irradiation field.

8. A method according to claim 1, wherein a recording of said at least one radiation image is performed on said recording medium which comprises a stimulable phosphor sheet.

9. A method of detecting one or more irradiation fields within a recording region of a recording medium on which is recorded one or more radiation images in said recording region, each radiation image being within at least one irradiation field, comprising the steps of:
designating a plurality of sections of said recording region as subdivisions, each subdivision being a potential irradiation field receiving region, no more than one irradiation field being found in each subdivision,
photoelectrically detecting image signals corresponding to recorded radiation images n said recording region,
from said image signals separately detecting for an irradiation field within each of said subdivisions, thereby independently determining the boundaries of an irradiation field which may be contained in each of said subdivisions.

10. A method as claimed in claim 9, wherein said recording medium is a stimulable phosphor sheet, and said step of photoelectrically detecting image signals comprises the steps of:
scanning said stimulable phosphor sheet with stimulating rays to cause said stimulable phosphor sheet to emit radiation proportional to the radiation images stored thereon,
detecting said emitted radiation, and
converting said detecting emitted radiation to said image signals.

11. A method according to claim 9, wherein said detecting step comprises for each subdivision:
detecting photoelectrically prospective edge points of said irradiation field;
connecting said prospective edge points of said irradiation field by passing lines through said prospective edge points of said irradiation field; and
recognizing said irradiation field as a region surrounded by one of said lines and said lines and an outer edge of said recording region.

12. A method according to claim 9, wherein said method further comprises a step of storing results of each detection of said electric image signals of said each subdivision in a memory means and combining the results of the separate detections.

13. A method according to claim 9, wherein said method further comprises a step of identifying a first irradiation field within a first subdivision merged with a second irradiation field in an adjacent, second subdivision.

14. A method according to claim 13, wherein said identifying step comprises the steps of:
encoding picture elements in picture elements rows on adjacent outer edges of said first and second subdivisions;
comparing the values of codes of opposed picture elements in opposed picture element rows of said first and second subdivisions; and
determining said first and second irradiation fields are merged based upon a number of opposed picture elements which are both in an irradiation field exceeding a predetermined percent of a number of all of said picture elements on said opposed picture element rows of said first and second small regions.

15. A method according to claim 13, wherein said identifying step is made based upon a distance apart of said first and second irradiation fields, said first and second irradiation fields being merged when said distance is smaller than a predetermined value.

16. A method according to claim 13, wherein said identifying step is made based upon an intercept and inclination of an equation representing an edge of said first irradiation field being substantially equal to those of an equation representing an edge of said second irradiation field.

17. A method according to claim 9, wherein a recording of said at least one radiation image is performed on said recording region which comprises a stimulable phosphor sheet.

18. An apparatus for detecting an irradiation portion of a recording region of a recording medium on which at least one radiation image is recorded with said irradiation portion being contained within said recording region, said irradiation portion being either a single irradiation field or a plurality of irradiation fields, the apparatus comprising:
scanning means for scanning said recording region to photoelectrically detect radiation images stored therein, said recording region emitting light in proportion to said radiation stored in said recording region;

detecting and converting means for detecting and converting photoelectrically said emitted light into image signals for each small region;

designating means for designating a plurality of sections of said recording region as subdivisions, each for receiving a single irradiation field; and processing means for independently processing said electric image signals corresponding to radiation detected from each of said subdivisions to detect the boundary of an irradiation field within each of said subdivisions.

19. An apparatus according to claim 18, wherein said detecting and converting means comprises a photomultiplier.

20. An apparatus according to claim 18, wherein said recording medium comprises a stimulable phosphor sheet.

* * * * *